United States Patent
Saito et al.

[19]

[11] Patent Number: 5,882,317
[45] Date of Patent: Mar. 16, 1999

[54] METHOD AND APPARATUS OF SAMPLING SUCTION EFFUSION FLUID

[75] Inventors: Soichi Saito; Yuji Kajiwara; Atsushi Saito, all of Tokyo, Japan

[73] Assignee: NEC Corporation, Japan

[21] Appl. No.: 934,159

[22] Filed: Sep. 19, 1997

[30] Foreign Application Priority Data

Sep. 20, 1996 [JP] Japan .................................. 8-250095

[51] Int. Cl.$^6$ ....................................................... A61B 5/00
[52] U.S. Cl. .......................................... 600/578; 606/167
[58] Field of Search ................................... 600/578, 573;
606/167, 172, 169, 181, 183, 185, 186;
604/21, 22

[56] References Cited

U.S. PATENT DOCUMENTS

| | | | |
|---|---|---|---|
| 4,619,256 | 10/1986 | Graybill et al. | 606/172 |
| 5,437,651 | 8/1995 | Todd et al. | 604/313 |
| 5,582,184 | 12/1996 | Erickson et al. | 606/181 |
| 5,746,217 | 5/1998 | Erickson et al. | 600/573 |
| 5,762,640 | 6/1998 | Kajiwara et al. | 600/573 |

FOREIGN PATENT DOCUMENTS

| | | |
|---|---|---|
| 4341241 | of 1992 | Japan . |
| 6-70934 | 3/1994 | Japan . |
| 7132119 | of 1995 | Japan . |
| 7-241774 | 9/1995 | Japan . |
| 8-308804 | 11/1996 | Japan . |

OTHER PUBLICATIONS

S. Murakami, et al., "A Study of Glucose Concentration Response in Suction Effusion Fluid Against Blood Glucose", the 35th Japan Soc. ME & BE Conference, May 1996, p. 474.

*Primary Examiner*—Max Hindenburg
*Assistant Examiner*—Pamela L. Wingood
*Attorney, Agent, or Firm*—Ostrolenk, Faber, Gerb & Soffen, LLP

[57] ABSTRACT

A method of sampling a suction effusion fluid is provided, which is convenient and highly efficient and which leaves no marks on the skin. First, (a) A suction cell with a cup-shaped hollow body is prepared. The body has an inner space, an aperture connected to the inner space, and a suction port connected to the inner space. The aperture is applied to a skin of a living organism. The inner space of the body is evacuated through the suction port. Next, (b) Bores are formed in a horny layer of the skin of the living organism. The bores has a depth that penetrates the horny layer and do not reach a capillary tube in the skin. Further, (c) The suction cell is held so that the aperture of the cell is opposed to the skin. The cell covers the bores formed in the horny layer and is tightly contacted with the skin. Finally, (d) The inner space of the suction cell is evacuated in such a way that the skin is bulged and the bores are expanded. Thus, the suction effusion fluid is sampled from the skin of the living organism through the suction cell.

20 Claims, 8 Drawing Sheets

METHOD AND APPARATUS OF SAMPLING SUCTION EFFUSION FLUID

BACKGROUND OF THE INVENTION

1. Field of the Invention

The present invention relates to a method and an apparatus of sampling a suction effusion fluid and more particularly, to a method of sampling a suction effusion fluid by sucking a body fluid from the skin surface of a human body for the purpose of determining the in-vivo substances, and a sampling apparatus used for the sampling method.

2. Description of the Related Art

A suction effusion fluid is an extremely small quantity of fluid obtained by vacuum-sucking a skin whose horny layer is removed. This fluid is considered to be an interstitial fluid in a subcutaneous tissue or a blood filtered and effused through the wall of a capillary.

In recent years, it has been clarified by many years of researches that the suction effusion fluid is a body fluid similar to a blood serum, and that the concentrations of some constituents such as glucose and lactic acid in the suction effusion fluid have a good correlation with the concentrations in the blood. This is disclosed in a paper, the 35th Japan Soc. ME & BE Conference, pp. 474, May, 1996, which was written by Murakami, Kaneyoshi, Nishida, Twasaki, Kawakami, Kayashima, Arai, and Kikuchi.

Because sampling of a suction effusion fluid is performed without viewing the blood, the physical and mental pain or a subject is little and the possibility of infection is low compared to those in blood drawing. Because the sampled suction effusion fluid contains no blood corpuscle constituents, the constituents of a body fluid can be continuously determined with ease without the need for a special treatment such as anticoagulation. Accordingly, if the suction effusion fluid is used for determination of the living organism related substances, there arises an advantage that the physical and mental pain associated with blood drawing is reduced and thus, the constituents of the body fluid of women and infants, with whom blood-gathering is difficult, can easily be determined.

Until recent years, sampling of the suction effusion fluid had been made after removing the horny layer by such a method as the tape stripping method. In this conventional method, however, there are a problem that much labor and time are required to remove the horny layer and that a time period of two weeks or so is required for regeneration of the tissue of the horny layer.

To solve this problem, an improved sampling method of a suction effusion fluid, which eliminates the need for removing the horny layer, has been offered. This method is disclosed in, for example, the Japanese Patent Application No. 7-241774 filed in September 1995.

FIG. 1 shows a sectional view of a sampling apparatus of a suction effusion fluid used with the improved method disclosed in the Japanese Patent Application No. 7-241774 filed in September 1995.

As shown in FIG. 1, this sampling apparatus is comprised of a suction cell 503 having a suction port 501 at one end and an aperture 502 at the other end, and a channel plate 504, fitted to the aperture 502. The aperture 502 is opposed to a human skin and the channel plate 504 is directly contacted with the skin on sampling.

On the side of the suction port 501 of the channel plate 504, a plurality of channel grooves 505 are radially formed from the center of the plate 504. A plurality of through holes 506 are formed to extend axially in the plate 504. The through holes 506 are connected to the channel grooves 505.

On the side of the aperture 502 of the channel plate 504, a plurality of protrusion needles 507 are formed. Each of the protrusion needles 507 is formed by a protruded edge of the plate 504 in the vicinity of a corresponding one of the through holes 506. The length of the needles 507 is approximately 50 $\mu$m, and the diameter of the through holes is in the range of 50 to 200 $\mu$m.

Sampling of an effusion fluid with this apparatus in FIG. 1 is made in the following way.

First, in a portion of the skin where an effusion fluid is to be sampled, the aperture 502 of the suction cell 503 is brought into tight contact with the horny layer. Then, the inside of the suction cell 503 is evacuated from the suction port 501. With this evacuation, the protrusion needles 507 bite the skin surface to pierce the horny layer and as a result, an interstitial fluid in the skin is effused through the horny layer as an effusion fluid. The sucked effusion fluid is collected to the suction port 501 through the holes 506 and the grooves 505, and is taken out to the outside of the suction cell 503.

The improved sampling method of a suction effusion fluid using the sampling apparatus shown in FIG. 1 eliminates the need for removal of the horny layer, and substantially shortens the pretreatment time in sampling and the time period until the tissue is regenerated. Therefore, the above problems of the conventional method that removes the horny layer are solved. However, this improved sampling method has the following problems.

A first problem is that a suction effusion fluid is effused with a low efficiency. One reason is that only the portions of the skin with which the through holes 506 are contacted are sucked and therefore, the area of the surface layer of the skin contributing to the effusion is small, when compared to that with the conventional method where the horny layer is removed. Another reason is that the gap between the protrusion needles 507 serving as an effusion path for the effusion fluid and the opposing horny layer is narrow, when compared to that with the conventional method.

A second problem is that penetration of the horny layer by the protrusion needles 507 tends to be insufficient. This is because the skin is deformed so that the piercing pressure is distributed, which results from the piercing of the needles 507 is made by a semi-static behavior consisting of pressing and suction.

SUMMARY OF THE INVENTION

Accordingly, an object of the present invention is to provide a method of sampling a suction effusion fluid that is convenient and highly efficient, and that leaves no marks on the skin.

Another object of the present invention is to provide an apparatus of sampling a suction effusion fluid that is capable of a convenient and highly-efficient sampling without leaving no marks on a skin.

The above objects together with others not specifically mentioned will become clear to those skilled in the art from the following description.

According to a first aspect of the present invention, a method of sampling a suction effusion fluid is provided, which is comprised of the following steps (a) to (d):

(a) A suction cell with a cup-shaped hollow body is prepared. The body has an inner space, an aperture connected to the inner space, and a suction port connected to the inner space. The aperture is applied to a skin of a living organism. The inner space of the body is evacuated through the suction port.

(b) Bores are formed in a horny layer of the skin of the living organism. The bores have a depth that penetrates the horny layer and do not reach a capillary tube in the skin.

(c) the suction cell is held so that the aperture of the cell is opposed to the skin. The cell covers the bores formed in the horny layer and is tightly contacted with the skin.

(d) The inner space of the suction cell is evacuated in such a way that the skin is bulged and the bores are expanded.

Thus, the suction effusion fluid is sampled from the skin of the living organism through the bores of the horny layer.

With the method of sampling of suction effusion fluid according to the first aspect of the present invention, bores are formed in a horny layer of a skin of a living organism. The bores has a depth that penetrates the horny layer and do not reach a capillary tube in the skin. Then, the suction cell is held so that the aperture of the cell is opposed to the skin. The cell covers the bores formed in the horny layer and is tightly contacted with the skin. Further, the inner space of the suction cell is evacuated in such a way that the skin is bulged and the bores are expanded.

Therefore, the suction effusion fluid is sampled from the skin of the living organism through the bores without removing the horny layer. This means that the sampling of a suction effusion fluid is accomplished conveniently and that no marks are left on the skin after the sampling is completed.

Additionally, because the inner space of the suction cell is evacuated after the bores are formed in the horny layer, the skin is bulged and the bores are expanded on sampling. As a result, the sampling is accomplished at a high efficiency.

In a preferred embodiment of the method according the first aspect, the bores are formed by piercing the skin with needles under application of vibration in an axial direction. There is an additional advantage that the formation of the bores is ensured even if the skin escapes.

In another preferred embodiment of the method according the first aspect, the depth of the bores is 0.5 mm or less. There is an additional advantage that the depth of the bores is readily controlled to penetrate the horny layer and not to reach the capillary tube in the skin.

According to a second aspect of the present invention, an apparatus of sampling a suction effusion fluid is provided, which is comprised of a piercing jig and a suction cell.

The piercing jig has needles for piercing a horny layer of a skin of a living organism to thereby form bores for sucking the suction effusion fluid. The bores are formed to penetrate the horny layer and not to reach a capillary tube in the skin.

The suction cell serves to such the suction effusion fluid from the living organism. The cell includes a cup-shaped hollow body having an inner space, an aperture connected to the inner space, and a suction port connected to the inner space. The aperture is applied to the skin of the living organism. The inner space of the body is evacuated through the suction port.

On sampling, the suction cell is held so that the aperture of the cell is opposed to the skin. The cell covers the bores formed in the horny layer and is tightly contacted with the skin. The inner space of the suction cell is evacuated through the suction port in such a way that the skin is bulged and the bores are expanded.

Thus, the suction effusion fluid is sampled from the skin of the living organism through the bores of the horny layer.

With the apparatus of sampling a suction effusion fluid according to the second aspect of the present invention, the bores are formed in the horny layer by using the piercing jig. The suction cell has the same configuration as that used in the method according to the first aspect.

Therefore, because of the same reason as that in the method according to the first aspect, a convenient and highly-efficient sampling is able to be accomplished without leaving no marks on the skin.

In a preferred embodiment of the apparatus according to the second aspect, the piercing jig has a vibration mechanism that produces axial vibration of the needles to ensure piercing of the needles into the skin. There is an additional advantage that the formation of the bores is ensured even if the skin escapes.

In another preferred embodiment of the apparatus according to the second aspect, the needles of the piercing jig are designed for forming the bores having a depth of 0.5 mm or less. There is an additional advantage that the depth of the bores is readily controlled to penetrate the horny layer and not to reach the capillary tube in the skin.

Typically, the body of the suction cell has a cylindrical shape so that the skin is sucked into the cylindrical inner space of the body through the circular aperture due to suction. This is a very simple configuration.

However, in still another preferred embodiment of the apparatus according to the second aspect, the body of the cell includes a hole plate fitted to the aperture. The hole plate has holes through which the skin is bulged and the bores are expanded. There is an additional advantage that the waiting time period is shortened, because the holes are smaller in size than the aperture of the body of the cell.

In a further preferred embodiment of the apparatus according to the second aspect, the body of the cell has a funnel shape so that the top of the inner space is curved semi-spherically. There is an additional advantage that the waiting time period is further shortened, because the remaining inner space of the body between the bulged skin and the inner wall of the body is very small.

The semi-spherical inner space may be formed in a spacer fitted to the aperture of the body, not in the body itself. In this case, since a plurality of semi-spherical inner spaces can be formed in the spacer, there is an additional advantage that the deformation of the skin is small on suction.

A sensor for determining the constituents of the suction effusion fluid may be integrally attached to the suction cell. In this case, there is an additional advantage that the waiting time period till the initial determination is minimized.

BRIEF DESCRIPTION OF THE DRAWINGS

In order that the invention may be readily carried into effect, it will now be described with reference to the accompanying drawings.

DETAILED DESCRIPTION OF THE PREFERRED EMBODIMENTS

Preferred embodiments of the present invention will be described below with reference to the drawings attached.

FIRST EMBODIMENT

A sampling apparatus of a suction effusion fluid according to a first embodiment of the present invention is shown in FIGS. 2 to 5. This apparatus includes a suction cell 1 and a piercing jig 20.

Figure 2:
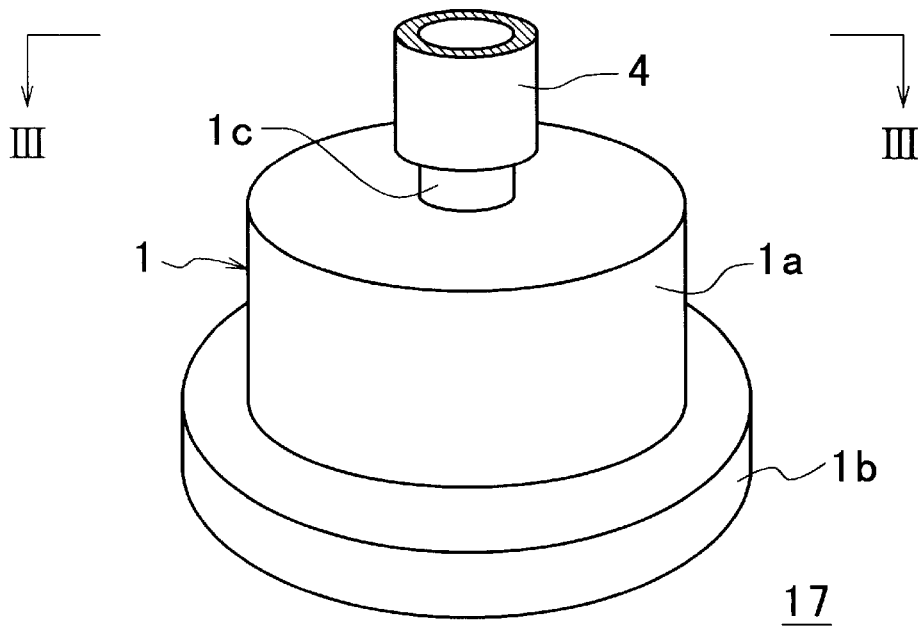
FIG. 2 is a perspective view of a suction cell of a sampling apparatus of a suction effusion fluid according to a first embodiment of the present invention.
Figure 3:
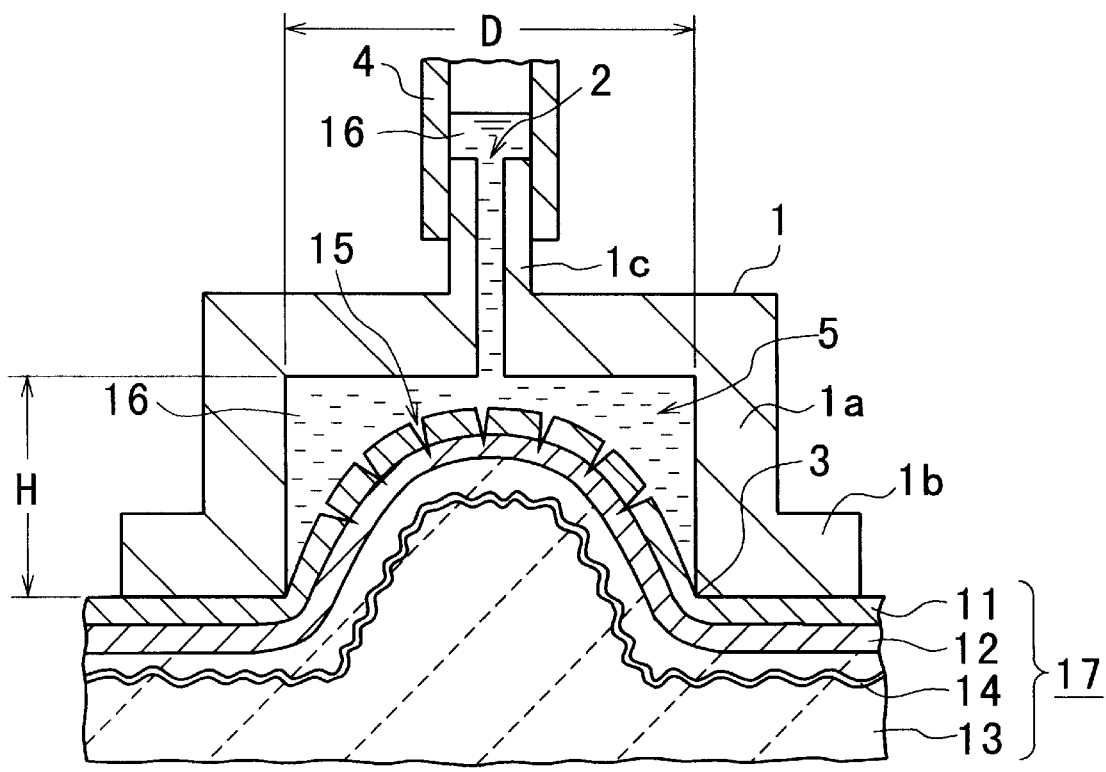
FIG. 3 is a schematic cross-sectional view of the suction cell of the apparatus according to the first embodiment, in which the cell is held to be opposed to a skin of a human body.

As shown in FIGS. 2 and 3, the suction cell 1 has a cylindrical body 1a, in which a cylindrical inner space 5 is formed. A circular flange 1b to be pressed against a skin 17 of a human body is formed at a lower end of the body 1a. A large-diameter circular aperture 3 to be contacted with the skin 17 is formed in the lower end of the body 1a. A suction port 2, which has a diameter smaller than the aperture 3, is formed at a protruding portion 1c formed at an upper end of the body 1a.

The size or diameter D of the suction cell 1 is determined to allow sampling of an effusion fluid 16 with a desired efficiency. To make the sampling at a rate of 1 $\mu$m/min, it is preferred that the aperture 3 is provided with a diameter of 5 mm or larger. Also, to eliminate the feeling of physical disorder when the suction cell 1 is loaded, it is desirable to set the diameter at a value as small as 50 mm at the maximum.

The height H of the suction cell 1 is preferably set so as to assure a space in which the skin 17 can sufficiently be bulged. Therefore, it is desirable to set the ratio (H/D) of the height H to the diameter D of the aperture 3 at approximately 2:1 to 1:2.

From the viewpoint of the living organism and productivity, the suction cell 1 is preferably made of a plastic material such as Teflon and vinyl chloride. However, the material is not limited to this.

A small-sized biosensor or a chemical sensor may be mounted to the suction cell 1. A small-sized sucking means such as a pipette, a vacuum suction tube, a hand pump, and a syringe may be integrally attached to the cell 1.

As clearly shown in FIG. 3, on sampling, the suction cell 1 is attached or loaded on the skin 17 to suck up the effusion fluid 16 through a tube 4 connected to the suction port 2. The skin 17, which is bulged by suction, is lodged into the inner space 5 of the cell 1. Bores 15 are formed in a horny layer 11 of the skin 17. Each of the bores 15 has a depth that reaches a seed layer 12 of the skin 17 but do not reach a true skin layer 13 of the skin 17. The seed layer 12 is an outer layer of the skin 17 excluding he horny layer 11.

In FIG. 3, the effusion fluid 16 effused from the bores 15 fills the remaining inner space 5 between the horny layer 11 and the inner top wall of the suction cell 1. The fluid 16 further fills the suction port 2 and a part of the tube 4.

Next, a treatment process or the skin 17, i.e., a formation process of the bores 15 will be described, which is carried out prior to a suction process.

Figure 4:
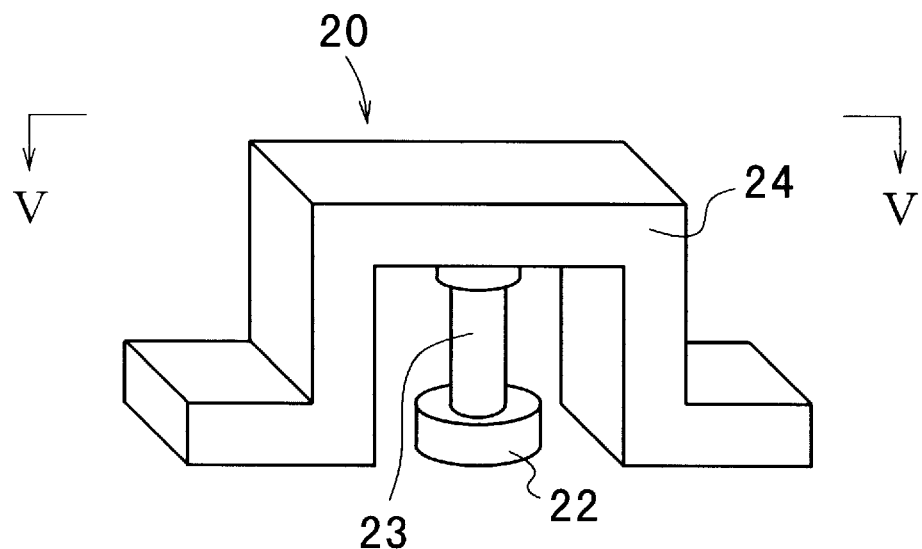
FIG. 4 is a perspective view of a piercing jig of the apparatus according to the first embodiment.
Figure 5:
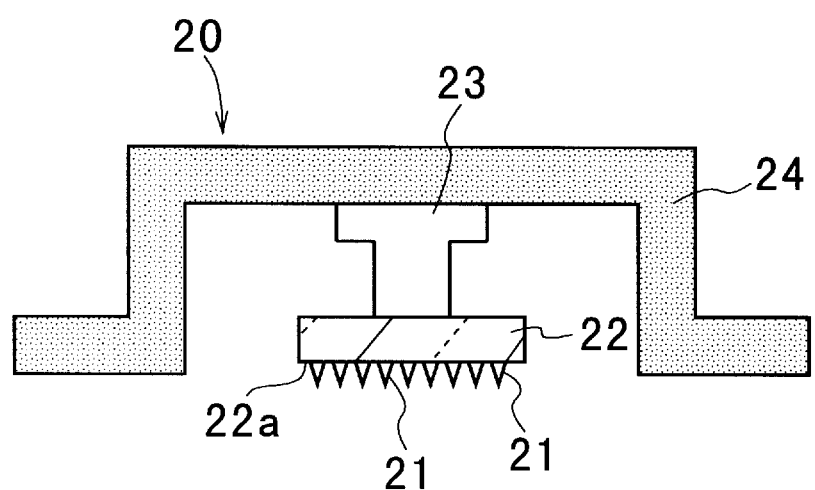
FIG. 5 is a schematic cross-sectional view of a piercing jig of the apparatus according to the first embodiment.

In this embodiment, the bores 15, which penetrate the horny layer 11 to reach the seed layer 12 but do not reach the true skin layer 13, are opened with the use of the piercing jig 20, as shown in FIGS. 4 and 5.

The jib 20 has a support 22 made of a circular plate. The support 22 holds needles 21 protruding from a lower surface 22a of the support 22. The support 22 serves as a stopper that restricts the penetration depth for the needles 21.

An upper end of the support 22 is connected to a vibration mechanism 23. The vibration mechanism 23 is supported by a strut 24. The level of the tips of the needles 21 is approximately the same as that of the bottom of the strut 24.

Generally, since the human skin 17 is rich in elastic force, shallow piercing of the skin 17 with the needles 21 will cause the skin 17 to escape. Therefore, there is the need for the vibration mechanism 23 to vibrate the needles 21 in an axial or vertical direction, causing surely the needles 21 to pierce the skin 17.

A piezoelectric actuator or a solenoid that produce vibrations at high speed and allows the amplitude to be precisely controlled is well suited for the vibration mechanism 23.

To treat the skin 17, the strut 24 is fixed onto the skin 17 and then, the needles 21 are brought into contact with or close to the horny layer 11. In this state, the vibration mechanism 23 is activated to cause the needles 21 to pierce the horny layer 11.

The effusion fluid 16 effused from each bore 15 is extremely small in quantity. Thus, it is desirable to set the density of the bores 15 at 100 or more per 1 $cm^2$ in order to efficiently sample the effusion fluid 16.

If the number of the needles 21 is too small, the piercing treatment must be made many times while changing the location. If the number of the needles 21 is too great, the piercing pressure per on needle is low, resulting in the impossibility of piercing. Therefore, it is proper to set the number of needles 21 at 10 to 1000.

The diameter of the treating section of the skin 17 need not be larger than that of the aperture 3 in the suction cell 1. If the vibration mechanism 23 is compact, a power supply and related components may be small-sized. Thus, it is recommended that the diameter of the aperture 3 in which the needles 21 are arranged be set at 50 mm or less.

When sampling from a front arm of a human body, it is recommended to set the length of the needles 21 at 0.05 to 0.8 mm, because the thickness of the horny layer 11 is 20 to 30 $\mu$m and that of the seed layer 12 is 30 to 40 $\mu$m.

When sampling from other portion or when a subject has a horny layer whose thickness is different from the standard one, it is recommended to use a piercing jig 20 having needles 21 with an appropriate, different length. Generally, the length of 0.03 to 1 mm can accommodate the variation in horny layer thickness.

By using such the piercing jig 20, the bore formation or skin treatment can be completed in 2 to 3 sec without bleeding. The needles 21 can smoothly pierce the skin 17, if the tip diameter is set at 1 to 5 $\mu$m and the tip angle at 15 to 45°.

Next, the mechanism for sampling the effusion fluid 16 will be described by referring to FIGS. 6A to 6C.

Figure 6A:
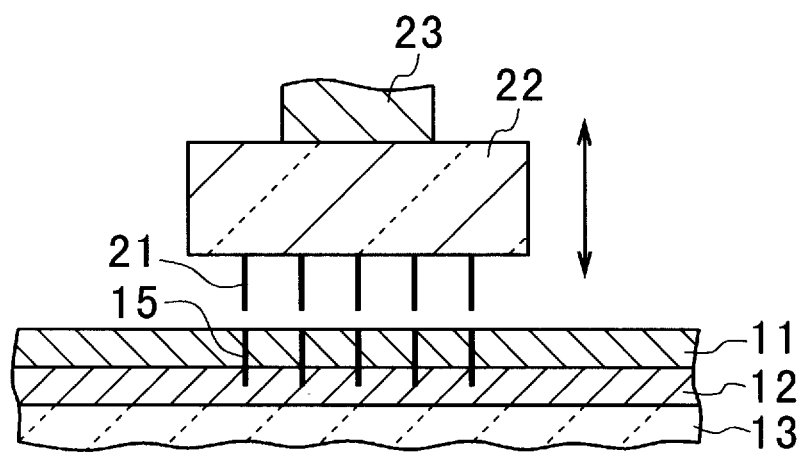
FIGS 6A and 6C are schematic cross-sectional views showing a sampling method of a suction effusion fluid according to the first embodiment, respectively.

In a portion where the effusion fluid 16 is to be sampled, the bores 15 are formed in the horny layer 11 by use of the piercing jig 20, as shown in FIG. 6A. This treatment is performed as follows.

First, the strut 24 of the piercing jig 20 is firmly held onto the skin 17. Then, the vibration mechanism 23 is activated to cause the needles 21 to pierce the horny layer 11. The arrow in the FIG. 6A indicates the direction of vibration applied to the needles 21.

If a piezoelectric actuator or a solenoid is used as the vibration mechanism 23, the needles 21 can be driven at high speed. For example, the needles 21 are vibrated at a rate of several tens Hz. Thus, the horny layer 11 is positively pierced. Since the bores 15 thus formed in the horny layer 11 are extremely small in area and shallow, the subject has no pains and the possibility of infection is extremely low.

Figure 6B:
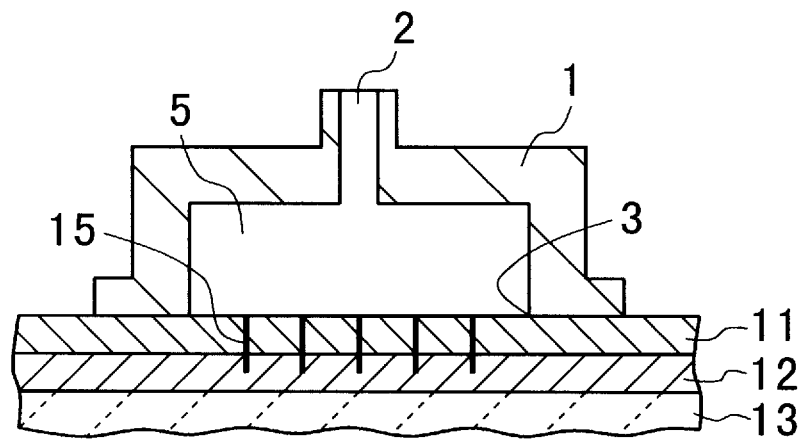
Figure 6C:
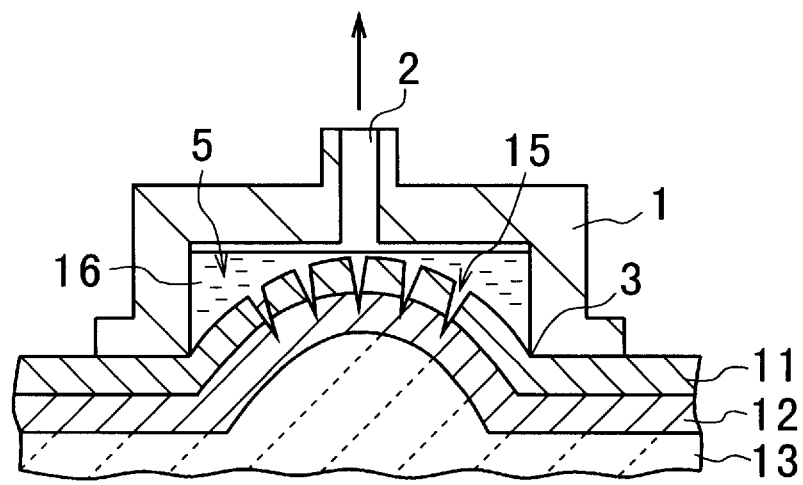

Next, as shown in FIG. 6B, the suction cell 1 is brought into tight contact with the skin 17. At this stage, the bores 15 are closed. Then, evacuation of the cell 1 for suction is performed through the suction port 2. This results in the skin 17 sucked into the inner space 5 of the suction cell 1, thereby bulging the skin and extending the bores 15, as shown in FIG. 6C. Consequently, the suction pressure is applied to the seed layer 12, which causes the effusion fluid 16 to be effused from the bores 15. The effusion fluid 16 fills the remaining space 5 between the inner wall of the cell 1 and the skin 17. Then, the fluid 16 is taken out to the outside of the cell 1 through the suction port 2.

As described above, with the sampling method according to the first embodiment, the effusion fluid 16 can be reliably sampled without removing the horny layer 11. In addition, the sampling efficiency can be increased to several times that for the conventional method.

Therefore, sampling can be made with no failure, and the time required for sampling can be shortened. Thus, the constituents of the body fluid of women and infants, with whom blood-gathering is difficult, can easily be determined.

Through the inventor's tests, the following results were obtained.

The sampling efficiency for the effusion fluid 16 at a suction pressure of −0.8 atm was approximately 5 $\mu$l/min, which is two or more times as high as that given by the method where the horny layer 11 is removed for sampling. Therefore, determination could be made at an interval of one minute from the time when approximately 30 minutes elapsed after the start of the suction. The sampling portion of the skin 17 became utterly inconspicuous in 10 minutes after the removal of the suction cell 1, and became indistinguishable from the surrounding horny layer 11.

In this way, the effusion fluid 16 was sampled with a sufficiently high efficiency without removing the horny layer 11. In addition, no scar was left on the skin 17.

SECOND EMBODIMENT

Figure 7:
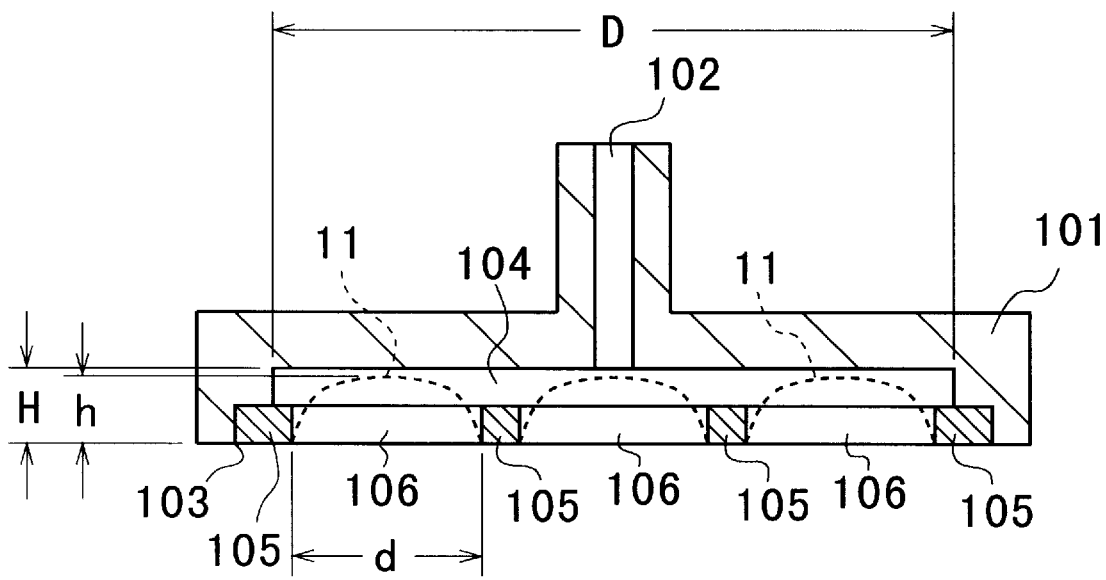
FIG. 7 is a schematic cross-sectional view of a suction cell of a sampling apparatus according to a second embodiment.

FIG. 7 shows a suction cell 101 of a sampling apparatus according to a second embodiment.

As shown in FIG. 7, this suction cell 101 is cylindrical, and has a large-diameter aperture 103 at the bottom end an a small-diameter suction port 102 at the top end. A disk-shaped hole plate 105 is fitted to the aperture 103.

With the suction cell 101, the ration (H/D) of the height H to the diameter D of the aperture 103 is higher than that for the first embodiment, which is approximately 1:10.

Between the hole plate 105 and the inner ceiling of the suction cell 101, a cylindrical inner space 104 is formed to accommodate the skin 17 bulged in suction.

Figure 8:
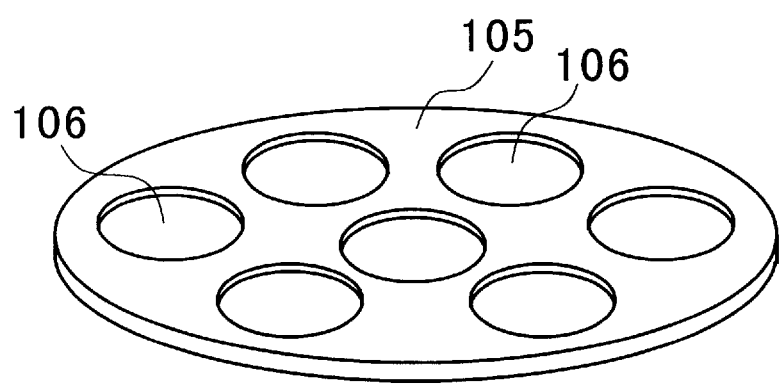
FIG. 8 is a perspective view of a hole plate of the suction cell of the apparatus according to the second embodiment.

As shown in FIG. 8, the hole plate 105 is a thin disk having a plurality of circular holes 106. The holes 106 has a same diameter d smaller than the diameter D of the aperture 103. This plate 105 may be made of plastic, metal, semiconductor, or other material. However, to prevent metal allergy of the subject, it is desirable to use a material such as Teflon, which is good in living organism suitability.

The dotted lines in FIG. 7 represents the horny layer 11 when the suction is made. The other components of the skin 17 are not shown for the sake of simplification. A suction means (not shown in FIG. 7) is connected to the suction port 102.

Because this suction cell 101 has a low height-to-diameter ratio (H/D), the volume of the inner space 104 is smaller than that for the sampling apparatus according to the first embodiment. Because the fluid 16 to fill up the inner space 104 cannot be taken out to the outside, the smaller the volume, the shorter the waiting time period from the start of the suction to the moment when the fluid 16 is taken out.

The inventors' test indicated that the waiting time period could be shortened to approximately (2/3) of that in the first embodiment.

THIRD EMBODIMENT

Figure 9:
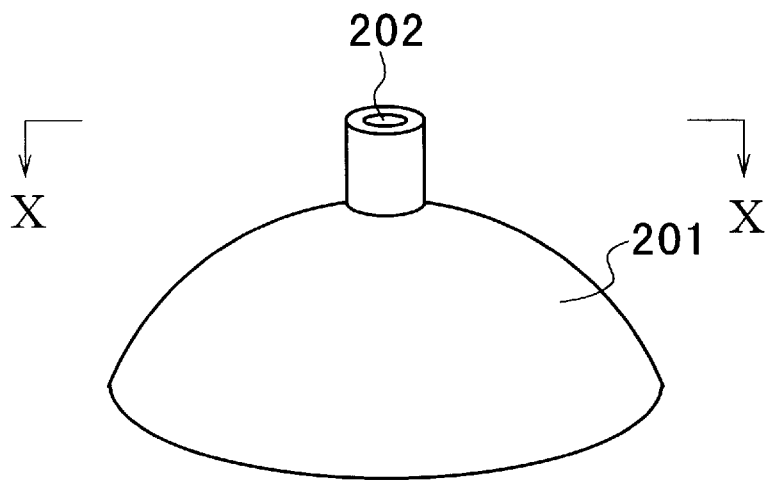
FIG. 9 is a perspective view of a suction cell of a sampling apparatus according to a third embodiment.
Figure 10:
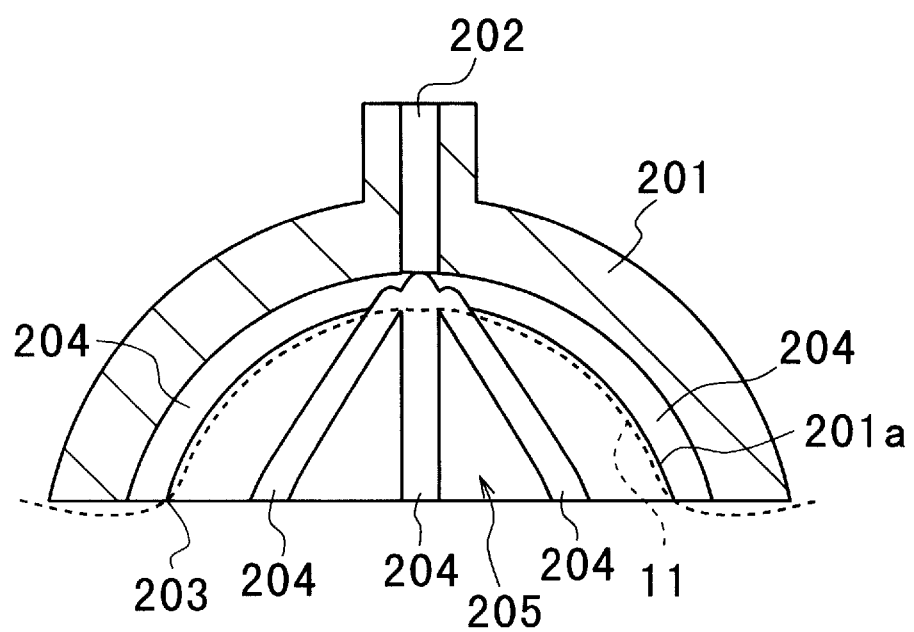
FIG. 10 is a schematic cross-sectional view of the suction cell of the apparatus according to the third embodiment.

FIGS. 9 and 10 show a suction cell of a sampling apparatus according to a third embodiment of the present invention.

As shown in FIG. 9, the suction cell 201 has a small-diameter suction port 202 a the top end and a large-diameter aperture 203 at the bottom end. The cell 201 is funnel-shaped, and the inner wall 201a of the cell 201 is curved semi-spherically. Radial grooves 204 connecting to the suction port 202 are formed on the semi-spherical inner wall 201a.

The dotted line in FIG. 10 indicates the horny layer 11 in an imagined suction, and the other skin tissues are not shown for simplification.

Next, the sampling mechanism will be described. The horny layer 11 with which bores 15 are formed is bulged by suction, and brought close to or into contact with the inner wall 201a of the suction cell 201. The effusion fluid 16 effused from the bores 15 is collected into the suction port 202 through the grooves 204, and taken out to the outside of the suction cell 201.

When the curvature radius of the inner wall 201a of the suction cell 201 is set at approximately the same as the radius of the aperture 203, the horny layer 11 is sufficiently extended while the gap is further decreased. This technique eliminates the gap between the horny layer 11 and the suction cell 201 except for the grooves 204. Therefore, the volume of the fluid 16, which does not contribute to the sampling and which is known as the "dead volume", is minimized.

The inventors' test indicated that the waiting time period from the start of the suction to the moment when the fluid 16 is taken out could be shortened to approximately (1/3) of that in the first embodiment.

Figure 11:
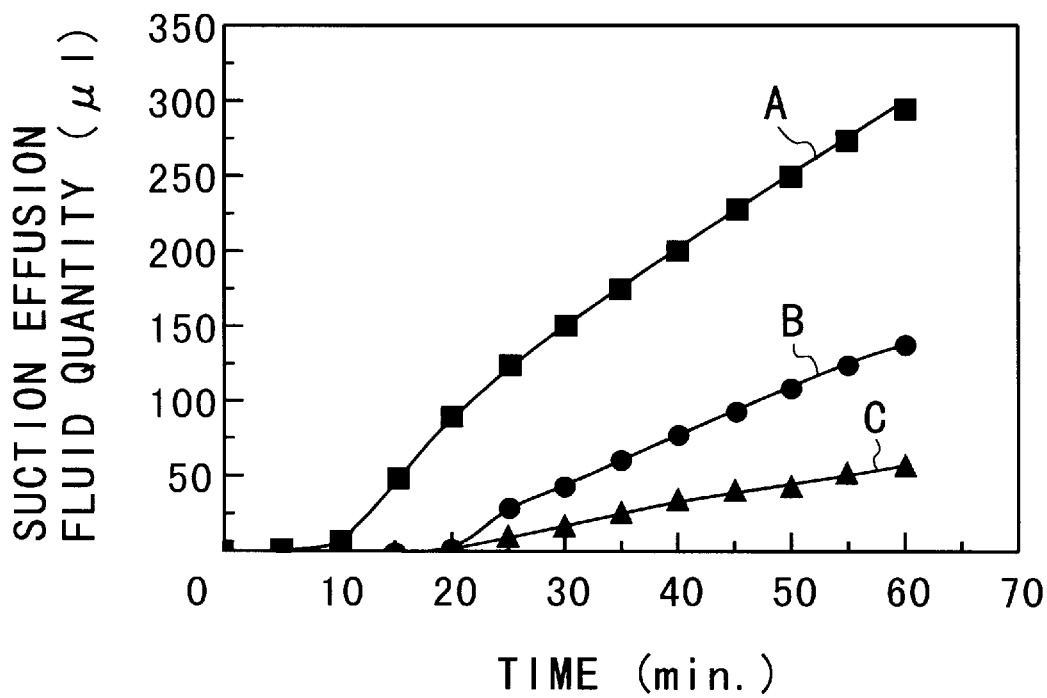
FIG. 11 is a graph showing the relationship of the fluid quantity with time, which is obtained by a sampling method according to the third embodiment.

The result (curve A) of sampling with the third embodiment is shown in FIG. 11 together with the result (curve B) by the conventional method removing the horny layer and the result (curve C) by the improved method disclosed in the Japanese Patent Application No. 7-241774.

Figure 1:
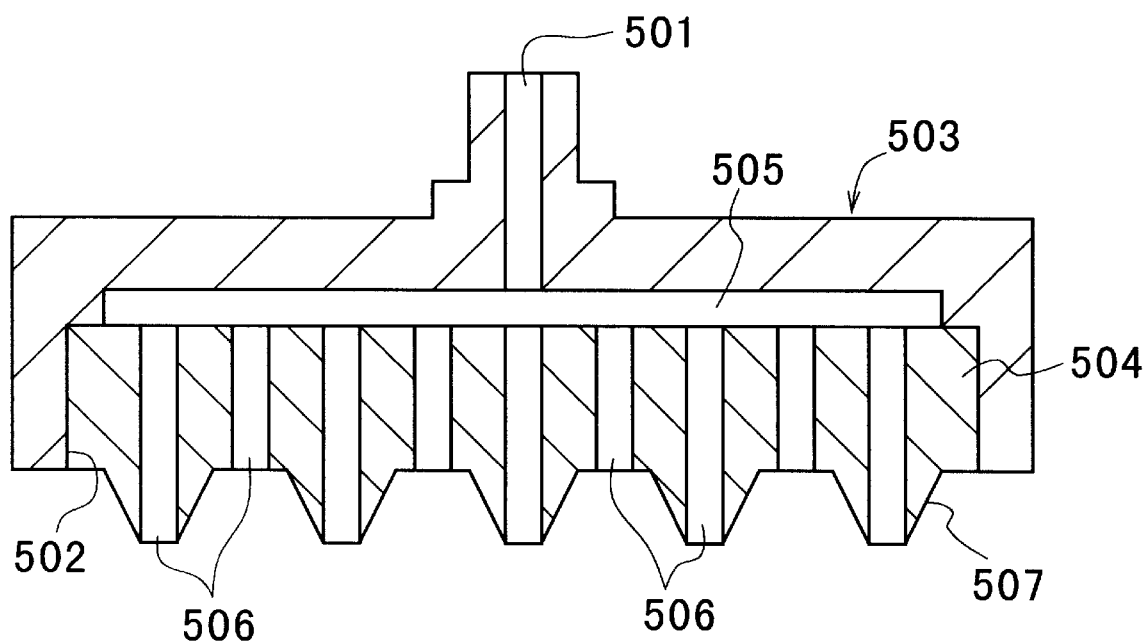
FIG. 1 is a schematic cross-sectional view of a sampling apparatus of a suction effusion fluid disclosed in the Japanese Patent Application No. 7-241774.

As seen from FIG. 11, with the third embodiment, the constituent determination could be made 30 minutes after the start of the suction, and the sampling efficiency was four times as high as that by the improved method as shown in FIG. 1, and two or more times as high as that by the conventional method where the horny substance is removed. Therefore, the constituent determination could continuously be made at an interval of 1 to 2 minutes with the third embodiment.

FOURTH EMBODIMENT

Figure 12:
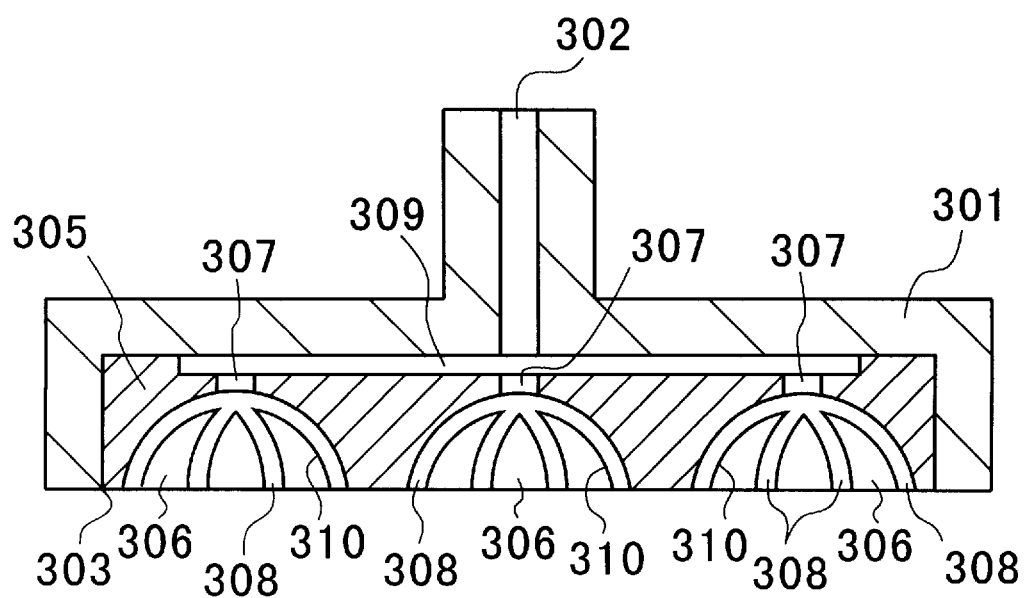
FIG. 12 is a schematic cross-sectional view of a suction cell of a sampling apparatus according to a fourth embodiment.

FIG. 12 shows a suction cell of a sampling apparatus according to a fourth embodiment of the present invention.

As shown in FIG. 12, the suction cell 301 has a configuration with which a disk-shaped space 305 is fitted to a cylindrical aperture 303 at the bottom end, and a suction port 302 is formed at the top end.

The spacer 305 is provided with a plurality of semispherical concavities 306. At the apex on the side of the suction port 302, through holes 307 are formed. On the inner wall of the concavities 306, radial grooves 308 connecting to the through holes 307 are provided. On the back of the spacer 305, radial channel grooves 309 extending from the center just under the suction port 302 and connecting to the respective through holes 307 are formed.

Next, the sampling mechanism will be described. When the suction cell 301 is loaded on the skin for suction, the skin 17 is bulged to be lodged in the respective concavities 306. Then, the effusion fluid 16 is effused from the bores 15. The effusion fluid 16 is collected to the through holes 307 through the grooves 308, and further collected to the suction port 302 through the channel grooves 309 before being taken out to the outside.

When the radius of the aperture of each concavity 306 shown in FIG. 12 is set at 2 to 10 mm, and the radius of curvature is set at approximately the same as the radius of the aperture 303 of the cell 301, the dead volume is minimized as with the third embodiment, resulting in a good sampling efficiency.

In addition, the suction apparatus of the fourth embodiment causes a minimum deformation of the skin. Thus, it offers an advantage that it can be used with a sense of security by a person having a weak skin.

FIFTH EMBODIMENT

Figure 13:
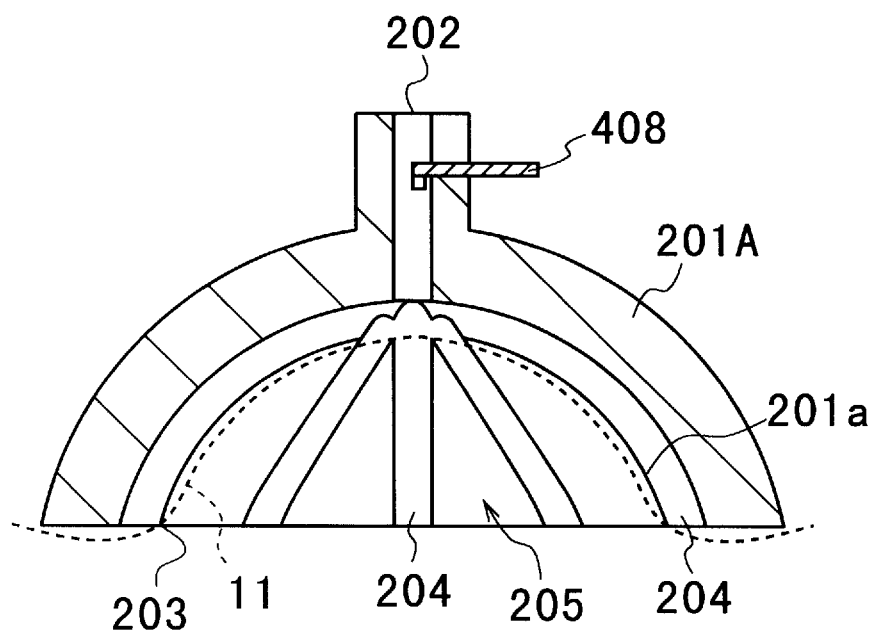
FIG. 13 is a schematic cross-sectional view of a suction cell of a sampling apparatus according to a fifth embodiment.

FIG. 13 shows a suction cell of a sampling apparatus according to a fifth embodiment of the present invention.

This suction cell 201A of the fifth embodiment is obtained by integrating the suction cell 201 according to the third embodiment in FIGS. 9 and 10 with a sensor 408 such as a biosensor and a chemical sensor for determining the constituents of the fluid 16.

With the apparatus according to the fifth embodiment, since the amount of fluid 16 that is required to fill a fluid feed system from the suction cell 201A to the sensor 408 is small, the waiting time period till the initial determination can be minimized.

In addition, the constituents that vary from one minute to the next as the effusion fluid 16 is effused can be continuously determined. To the sensor 408, such a component as a cable, a detector circuit, and an indicator is connected although they are not shown.

As a sensor, such a biosensor as a glucose sensor, a urea sensor, and a lactic acid sensor, or a chemical sensor, such as a pH sensor, a $Na^+$ sensor, a $K^+$ sensor, a $Cl^-$ sensor, $pO_2$ sensor, $pCO_2$ sensor, and an ammonia sensor may be used.

The sampling apparatus according to the fifth embodiment, to which the sensor 408 is added, can be manufactured by using any of the suction cells in the above first to fourth embodiments.

While the preferred forms of the present invention has been described, it is to be understood that modifications will be apparent to those skilled in the art without departing from the spirit of the invention. The scope of the invention, therefore, is to be determined solely by the following claims.

What is claimed is:

1. A sampling method of a suction effusion fluid, the method comprising the steps of:
   (a) preparing a suction cell with a cup-shaped hollow body;
   said body having an inner space, an aperture connected to said inner space, and a suction port connected to said inner space;
   said aperture being applied to a skin of a living organism;
   said inner space of said body being evacuated through said suction port;
   (b) forming bores in a horny layer of said skin of said living organism;
   said bores having a depth that penetrates said horny layer and do not reach a capillary tube in said skin;
   (c) holding said suction cell so that said aperture of said cell is opposed to said skin;
   said cell covering said bores formed in said horny layer and being tightly contacted with said skin; and
   (d) evacuating said inner space of said suction cell in such a way that said skin is bulged and said bores are expanded;
   wherein said suction effusion fluid is sampled from said skin of said living organism through said bores of said horny layer.

2. A method as claimed in claim 1, wherein said bores are formed by piercing said skin with needles under application of vibration in an axial direction.

3. A method as claimed in claim 1, wherein the depth of said bores is 0.5 mm or less.

4. A sampling apparatus of a suction effusion fluid, said apparatus comprising:
   (a) a piercing jig having needles for piercing a horny layer of a skin of a living organism to thereby form bores for sucking said suction effusion fluid;
   said bores being formed to penetrate said horny layer and not to reach a capillary tube in said skin; and
   (b) a suction cell for sucking said suction effusion fluid from said living organism;
   said cell including a cup-shaped hollow body;
   said body having an inner space, an aperture connected to said inner space, and a suction port connected to said inner space;
   said aperture being applied to said skin of said living organism;
   said inner space of said body being evacuated through said suction port;
   wherein on sampling, said suction cell is held so that said aperture of said cell is opposed to said skin;
   and wherein said cell covers said bores formed in said horny layer and is tightly contacted with said skin;
   and wherein said inner space of said suction cell is evacuated through said suction port in such a way that said skin is bulged and said bores are expanded;
   and wherein said suction effusion fluid is sampled from said skin of said living organism through said bores of said horny layer.

5. An apparatus as claimed in claim 4, wherein each of said piercing jig has a vibration mechanism that produces axial vibration of said needles to ensure piercing of said needles into said skin.

6. An apparatus as claimed in claim 4, wherein said needles of said piercing jig are designed for forming said bores having a depth of 0.5 mm or less.

7. An apparatus as claimed in claim 4, wherein said body of said suction cell has a cylindrical shape so that said skin is sucked into said cylindrical inner space of said body through said circular aperture due to suction.

8. An apparatus as claimed in claim 4, wherein said body of said cell includes a hole plate fitted to said aperture;

and wherein said hole plate has holes through which said skin is bulged and said bores are expanded.

9. An apparatus as claimed in claim 4, wherein said body of said cell has a funnel shape so that the top of said inner space is curved semi-spherically.

10. An apparatus as claimed in claim 4, further comprising a spacer having a semi-spherical inner space;

said spacer is fitted to said aperture of said body.

11. An apparatus as claimed in claim 4, further comprising a sensor for determining the constituents of said suction effusion fluid;

wherein said sensor is integrally attached to said cell.

12. An apparatus as claimed in claim 4, wherein each of said needles of said piercing jig has a tip diameter of 1 to 5 $\mu$m and a tip angle of 15 to 45°.

13. An apparatus as claimed in claim 4, wherein said needles are pierced under application of vibration in an axial direction.

14. An apparatus as claimed in claim 4, wherein said opening of said suction cell is of a circular with a diameter of 5 mm to 50 mm, or a polygonal shape with an area equivalent to said circular shape.

15. An apparatus as claimed in claim 4, wherein said suction cell has an inner wall that is curved in a circular arc and provided with radial grooves.

16. An apparatus as claimed in claim 4, wherein said suction cell has a spacer with through holes in an opening.

17. An apparatus as claimed in claim 16, wherein said spacer has an opening rate of 20% or higher.

18. An apparatus as claimed in claim 16, wherein the number of said through holes in said spacer ranges from 2 to 20.

19. An apparatus as claimed in claim 16, wherein said spacer has a semi-spherical space on a back side of said through hole, and a wall surrounding said semi-spherical space is provided with radial grooves connecting to said through hole.

20. An apparatus as claimed in claim 16, wherein said suction cell has radial channel grooves connecting to said through holes.

* * * * *